(12) United States Patent
Reed et al.

(10) Patent No.: US 9,427,566 B2
(45) Date of Patent: Aug. 30, 2016

(54) IMPLANTABLE NEUROSTIMULATION LEAD FOR HEAD PAIN

(71) Applicant: Syntilla Medical LLC, Dallas, TX (US)

(72) Inventors: Kenneth Lyle Reed, Dallas, TX (US); Robert Raymond Bulger, Dallas, TX (US)

(73) Assignee: Syntilla Medical LLC, Dallas, TX (US)

( * ) Notice: Subject to any disclaimer, the term of this patent is extended or adjusted under 35 U.S.C. 154(b) by 0 days.

(21) Appl. No.: 14/460,111

(22) Filed: Aug. 14, 2014

(65) Prior Publication Data

US 2015/0051678 A1 Feb. 19, 2015

Related U.S. Application Data

(60) Provisional application No. 61/865,893, filed on Aug. 14, 2013.

(51) Int. Cl.
*A61N 1/05* (2006.01)

(52) U.S. Cl.
CPC ........... *A61N 1/0526* (2013.01); *A61N 1/0504* (2013.01)

(58) Field of Classification Search
None
See application file for complete search history.

(56) References Cited

U.S. PATENT DOCUMENTS

| | | | |
|---|---|---|---|
| 4,819,647 A | 4/1989 | Byers | |
| 5,000,194 A | 3/1991 | Van Den Honert et al. | |
| 5,037,497 A | 8/1991 | Stypulkowski | |
| 5,215,086 A | 6/1993 | Terry, Jr. et al. | |
| 5,545,219 A | 8/1996 | Kuzma | |
| 6,016,449 A | 1/2000 | Fischell et al. | |
| 6,178,353 B1 | 1/2001 | Griffith et al. | |
| 6,236,892 B1 | 5/2001 | Feler | |
| 6,246,911 B1 | 6/2001 | Seligman | |
| 6,529,774 B1 * | 3/2003 | Greene | 600/545 |
| 6,597,954 B1 | 7/2003 | Pless et al. | |
| 6,606,521 B2 | 8/2003 | Paspa et al. | |
| 6,618,623 B1 | 9/2003 | Pless et al. | |
| 6,662,055 B1 * | 12/2003 | Prutchi | A61N 1/056 607/122 |

(Continued)

FOREIGN PATENT DOCUMENTS

| | | |
|---|---|---|
| EP | 0007157 | 1/1980 |
| WO | 2009158389 | 12/2009 |

OTHER PUBLICATIONS

Weiner RL and Reed KL. Peripheral neurostimulation for control of intractable occipital neuralgia. Neuromodulation :Journal of the International Neuromodulation Society. 1999; 2: 217-21.

(Continued)

*Primary Examiner* — Brian T Gedeon
(74) *Attorney, Agent, or Firm* — Howison & Arnott, LLP

(57) ABSTRACT

An implantable peripheral neurostimulation lead for head pain is adapted for implantation in the head for the therapeutic purpose of treating chronic head and/or face pain. The lead may include an extended lead body, a plurality of internal electrically conducting metal wires running along at least a portion of its length and individually connecting to a proximal surface contact and a distal surface electrode; a distal extended metal surface electrode array, subdivided into a plurality of sub-arrays; and a proximal in-line connector, which may include a proximal surface contact array adapted to couple with a separate implantable pulse generator. The lead may be operable to provide medically acceptable therapeutic neurostimulation to multiple regions of the head, including the frontal, parietal, and occipital regions of the head simultaneously.

17 Claims, 9 Drawing Sheets

(56) References Cited

U.S. PATENT DOCUMENTS

| | | | |
|---|---|---|---|
| 6,895,283 B2 | 5/2005 | Erickson et al. | |
| 6,920,359 B2 | 7/2005 | Meadows et al. | |
| 7,082,335 B2* | 7/2006 | Klein et al. | 607/126 |
| 7,127,298 B1 | 10/2006 | He et al. | |
| 7,315,763 B2* | 1/2008 | Kuzma | A61N 1/0541 607/137 |
| 7,319,906 B2 | 1/2008 | Kuzma et al. | |
| 7,437,197 B2 | 10/2008 | Harris et al. | |
| 7,499,755 B2 | 3/2009 | Cross, Jr. | |
| 7,676,273 B2 | 3/2010 | Goetz et al. | |
| 7,729,781 B2 | 6/2010 | Swoyer et al. | |
| 7,769,461 B2 | 8/2010 | Whitehurst et al. | |
| 7,894,905 B2 | 2/2011 | Pless et al. | |
| 8,027,735 B1 | 9/2011 | Tziviskos et al. | |
| 8,140,152 B2 | 3/2012 | John et al. | |
| 8,412,334 B2 | 4/2013 | Whitehurst et al. | |
| 8,504,163 B1 | 8/2013 | Meadows | |
| 8,509,876 B2 | 8/2013 | Karmarkar | |
| 8,538,545 B2 | 9/2013 | Meskens | |
| 8,543,212 B2 | 9/2013 | Merfeld et al. | |
| 8,634,909 B2 | 1/2014 | Zimmerling et al. | |
| 8,639,344 B2 | 1/2014 | Greenberg et al. | |
| 8,649,880 B1 | 2/2014 | Parker | |
| 8,718,779 B2 | 5/2014 | Whitehurst et al. | |
| 8,774,924 B2 | 7/2014 | Weiner | |
| 8,958,880 B2 | 2/2015 | De Giorgio | |
| 8,972,015 B2 | 3/2015 | Stack et al. | |
| 9,020,589 B2 | 4/2015 | Torgerson | |
| 9,095,699 B2 | 8/2015 | Rosenberg et al. | |
| 9,101,732 B2 | 8/2015 | Dadd et al. | |
| 2002/0116042 A1 | 8/2002 | Boling | |
| 2005/0102006 A1 | 5/2005 | Whitehurst et al. | |
| 2005/0182470 A1 | 8/2005 | Cross | |
| 2005/0209667 A1 | 9/2005 | Erickson et al. | |
| 2006/0241717 A1 | 10/2006 | Whitehurst et al. | |
| 2006/0247754 A1 | 11/2006 | Greenberg et al. | |
| 2006/0293723 A1 | 12/2006 | Whitehurst et al. | |
| 2007/0073357 A1 | 3/2007 | Rooney et al. | |
| 2007/0112404 A1 | 5/2007 | Mann et al. | |
| 2007/0203545 A1 | 8/2007 | Stone et al. | |
| 2008/0039916 A1 | 2/2008 | Colliou et al. | |
| 2008/0183253 A1 | 7/2008 | Bly | |
| 2008/0269716 A1 | 10/2008 | Bonde | |
| 2009/0018619 A1 | 1/2009 | Skelton et al. | |
| 2009/0210028 A1 | 8/2009 | Rigaux | |
| 2009/0312769 A1 | 12/2009 | Dadd | |
| 2010/0274313 A1 | 10/2010 | Boling et al. | |
| 2010/0331922 A1 | 12/2010 | DiGiore et al. | |
| 2011/0009925 A1 | 1/2011 | Leigh et al. | |
| 2011/0093047 A1 | 4/2011 | Davis et al. | |
| 2011/0112603 A1 | 5/2011 | Degiorgio et al. | |
| 2011/0160820 A1* | 6/2011 | Jackson et al. | 607/116 |
| 2011/0172736 A1 | 7/2011 | Gefen et al. | |
| 2011/0230935 A1* | 9/2011 | Zdeblick | 607/59 |
| 2012/0078327 A1 | 3/2012 | Sloan et al. | |
| 2012/0215218 A1 | 8/2012 | Lipani | |
| 2012/0277823 A1 | 11/2012 | Gerber et al. | |
| 2013/0085561 A1 | 4/2013 | Mashiach | |
| 2013/0238067 A1 | 9/2013 | Baudino | |
| 2013/0282086 A1 | 10/2013 | McDonald et al. | |
| 2013/0333918 A1 | 12/2013 | Lotfi | |
| 2014/0012349 A1 | 1/2014 | Zimmerling | |
| 2014/0142669 A1 | 5/2014 | Cook et al. | |
| 2014/0148883 A1 | 5/2014 | Stack et al. | |
| 2014/0222125 A1 | 8/2014 | Glenn et al. | |
| 2014/0303685 A1 | 10/2014 | Rosenberg et al. | |
| 2014/0343626 A1 | 11/2014 | Thenuwara et al. | |
| 2015/0025613 A1 | 1/2015 | Nyberg, II et al. | |
| 2015/0087892 A1 | 3/2015 | Tourrel et al. | |
| 2015/0157862 A1 | 6/2015 | Greenberg et al. | |

OTHER PUBLICATIONS

Goadsby PJ and Sprenger T. Current practice and future directions in the prevention and acute management of migraine. The Lancet Neurology. 2010; 9: 285-98.

Dodick DW. Occipital nerve stimulation for chronic cluster headache. Advanced Studies in Medicine. 2003; 3: S569-S71.

Saper JR, Dodick DW, Silberstein SD, McCaville S, Sun M and Goadsby PJ. Occipital nerve stimulation for the treatment of intractable chronic migraine headache: ONSTIM feasibility study. Cephalalgia : an international journal of headache. 2011; 31: 271-85.

Silberstein S, Dodick DW, Reed KL, et al. Safety and efficacy of peripheral nerve stimulation of the occipital nerves for the management of chronic migraine: Results from a randomized, multicenter, double-blinded, controlled study. Cephalalgia : An international journal of headache. 2012.

Slavin KV, Colpan ME, Munawar N, Wess C and Nersesyan H. Trigeminal and occipital peripheral nerve stimulation for craniofacial pain: a single-institution experience and review of the literature. Neurosurgical focus. 2006; 21: E5.

Schwedt TJ, Dodick DW, Hentz J, Trentman TL and Zimmerman RS. Occipital nerve stimulation for chronic headache—long-term safety and efficacy. Cephalalgia : an international journal of headache. 2007; 27: 153-7.

Reed KL, Black SB, Banta CJ, 2nd and Will KR. Combined occipital and supraorbital neurostimulation for the treatment of chronic migraine headaches: initial experience. Cephalalgia : an international journal of headache. 2010; 30: 260-71.

Reed KL, Will KR, Chapman J and Richter E. Combined occipital and supraorbital neurostimulation for chronic migraine headaches: an extended case series [abst]. 15th Congress of the International Headache Society. Berlin, Germany: Cephalalgia, 2011, p. 98-99.

Lipton RB, Goadsby PJ, Cady RK, et al. Prism study: occipital nerve stimulation for treatment—refractory migraine (p. abs). Cephalalgia : an international journal of headache. 2009; 29: 30.

Reed KL. Peripheral neuromodulation and headaches: history, clinical approach, and considerations on underlying mechanisms. Current pain and headache reports. 2012; 17: 25-35.

Mueller OM, Gaul C, Katsarava Z, Diener HC, Sure U and Gasser T. Occipital nerve stimulation for the treatment of chronic cluster headache —lessons learned from 18 months experience. Central European neurosurgery. 2011; 72: 84-9.

PCT: International Search Report and Written Opinion of PCT/US14/51235 (related application); Feb. 19, 2015; 24 pgs.

Medtronic, Inc. Peripheral Nerve Stimulation: Percutaneous Lead Implantation Guide for Treatment of Chronic Pain Jan. 1, 1999.

* cited by examiner

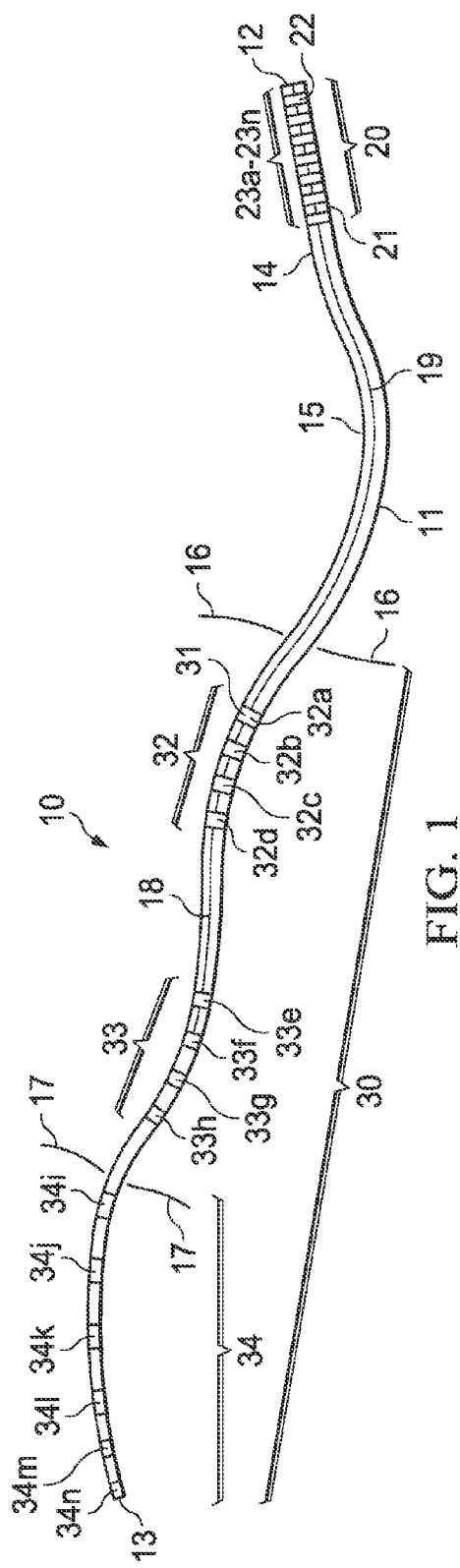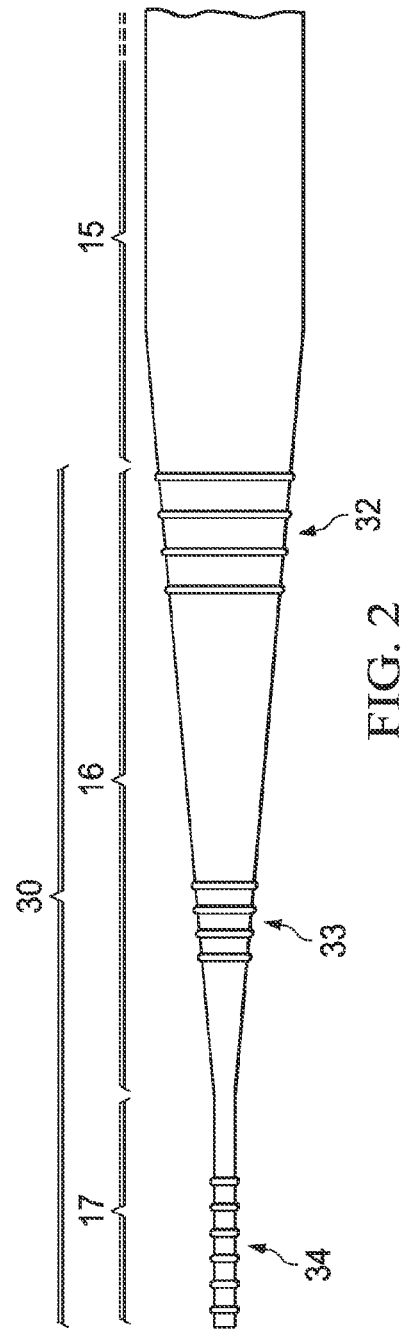

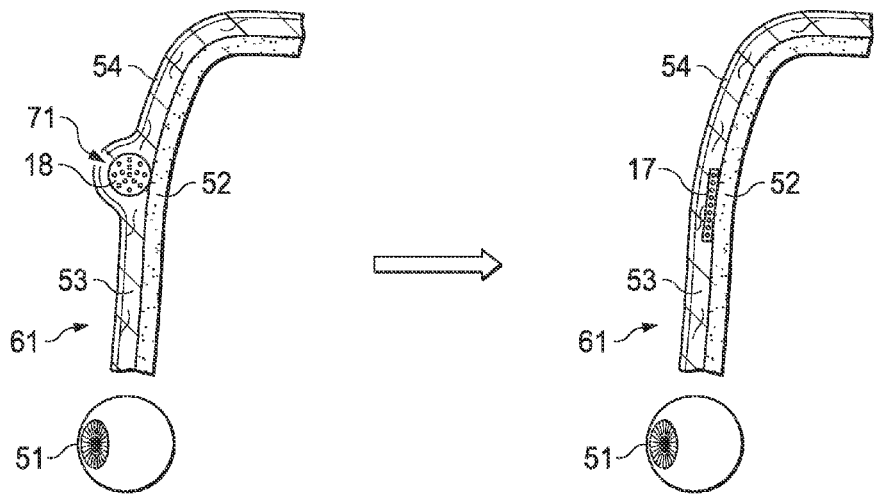
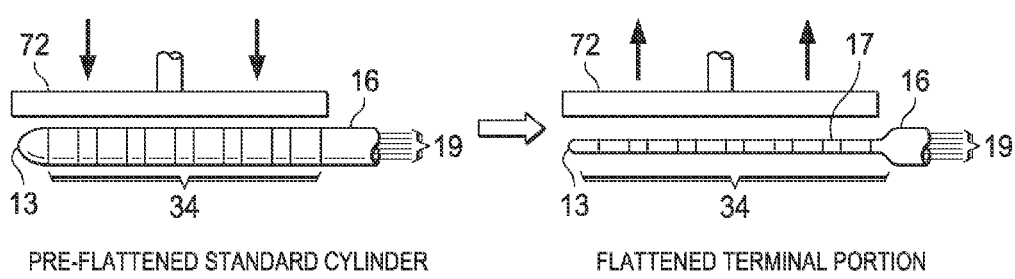
FIG. 12

FIG. 13

FIGURES LEGEND

- 10 LEAD BODY
  - 11 PLASTIC BODY MEMBER
  - 12 PROXIMAL END
  - 13 DISTAL END
  - 14 PROXIMAL LEAD BODY
  - 15 CENTRAL LEAD BODY
  - 16 TAPERED DISTAL LEAD BODY
  - 17 FLATTENED TERMINAL LEAD BODY
  - 18 INTERNAL WIRE
  - 19 SET OF ALL INTERNAL WIRES
    - 19a FIRST INTERNAL WIRE
    - 19b SECOND INTERNAL WIRE
    - 19c THIRD INTERNAL WIRE
    - 19d FOURTH INTERNAL WIRE
    - 19e FIFTH INTERNAL WIRE
    - 19f SIXTH INTERNAL WIRE
    - 19g SEVENTH INTERNAL WIRE
    - 19h EIGHTH INTERNAL WIRE
    - 19i NINTH INTERNAL WIRE
    - 19j TENTH INTERNAL WIRE
    - 19k ELEVENTH INTERNAL WIRE
    - 19l TWELFTH INTERNAL WIRE
    - 19m THIRTEENTH INTERNAL WIRE
    - 19n FOURTEENTH INTERNAL WIRE
- 20 PROXIMAL IN-LINE CONNECTOR
  - 21 SEMI-RIGID PLASTIC COVER
  - 22 SURFACE METAL CONTACT
  - 23 PROXIMAL CONTACT ARRAY
    - 23a FIRST SURFACE METAL CONTACT
    - 23b SECOND SURFACE METAL CONTACT
    - 23c THIRD SURFACE METAL CONTACT
    - 23d FOURTH SURFACE METAL CONTACT
    - 23e FIFTH SURFACE METAL CONTACT
    - 23f SIXTH SURFACE METAL CONTACT
    - 23g SEVENTH SURFACE METAL CONTACT
    - 23h EIGHTH SURFACE METAL CONTACT
    - 23i NINTH SURFACE METAL CONTACT
    - 23j TENTH SURFACE METAL CONTACT
    - 23k ELEVENTH SURFACE METAL CONTACT
    - 23l TWELFTH SURFACE METAL CONTACT
    - 23m THIRTEENTH SURFACE METAL CONTACT
    - 23n FOURTEENTH SURFACE METAL CONTACT
- 30 TERMINAL ELECTRODE ARRAY
  - 31 SURFACE METAL ELECTRODE
  - 32 PROXIMAL ELECTRODE ARRAY
    - 32a FIRST PROXIMAL SURFACE METAL ELECTRODE
    - 32b SECOND PROXIMAL SURFACE METAL ELECTRODE
    - 32c THIRD PROXIMAL SURFACE METAL ELECTRODE
    - 32d FOURTH PROXIMAL SURFACE METAL ELECTRODE
  - 33 MIDDLE ELECTRODE ARRAY
    - 33e FIRST MIDDLE SURFACE METAL ELECTRODE
    - 33f SECOND MIDDLE SURFACE METAL ELECTRODE
    - 33g THIRD MIDDLE SURFACE METAL ELECTRODE
    - 33h FOURTH MIDDLE SURFACE METAL ELECTRODE
  - 34 DISTAL ELECTRODE ARRAY
    - 34i FIRST DISTAL SURFACE METAL ELECTRODE
    - 34j SECOND DISTAL SURFACE METAL ELECTRODE
    - 34k THIRD DISTAL SURFACE METAL ELECTRODE
    - 34l FOURTH DISTAL SURFACE METAL ELECTRODE
    - 34m FIFTH DISTAL SURFACE METAL ELECTRODE
    - 34n SIXTH DISTAL SURFACE METAL ELECTRODE
- 40 NERVES OF THE HEAD
  - 41 GREATER OCCIPITAL NERVE
  - 42 LESSER OCCIPITAL NERVE
  - 43 THIRD OCCIPITAL NERVE
  - 44 POSTERIOR AURICULAR NERVE
  - 45 AURICULOTEMPORAL NERVE
  - 46 SUPRAORBITAL NERVE
- 50 STRUCTURES OF THE HEAD
  - 51 EYE
  - 52 BONEY SKULL
  - 53 SUBCUTANEOUS TISSUE
  - 54 SKIN
- 60 REGIONS OF THE HEAD
  - 61 SUPRAORBITAL REGION
  - 62 PARIETAL REGION
  - 63 OCCIPITAL REGION
  - 64 AURICULOTEMPORAL REGION
  - 65 INFRAORBITAL REGION
  - 66 MANDIBULAR REGION
  - 67 FOREHEAD MIDLINE
  - 68 C1 MIDLINE
  - 69 JUNCTION OF LATERAL FOREHEAD AND ANT PARIETAL
- 70 MISCELLANEOUS
  - 71 STANDARD CYLINDRICAL DISTAL LEAD BODY
  - 72 THERMO-MECHANICAL LEAD COMPRESSION

IMPLANTABLE NEUROSTIMULATION LEAD FOR HEAD PAIN

CROSS-REFERENCE TO RELATED APPLICATIONS

This application claims benefit of U.S. Provisional Application No. 61/865,893, filed Aug. 14, 2013, entitled IMPLANTABLE NEUROSTIMULATION LEAD FOR HEAD PAIN, the specification of which is incorporated by reference herein in its entirety. This application is related to U.S. patent application Ser. No. 14/460,139, now U.S. Pat. No. 9,042,991, filed of even date herewith, entitled IMPLANTABLE HEAD MOUNTED NEURO STIMULATION SYSTEM FOR HEAD PAIN, which claims benefit of U.S. Provisional Application No. 61/894,795, filed Oct. 23, 2013, the specification of which is incorporated by reference herein in its entirety.

TECHNICAL FIELD

The present disclosure relates to implantable neurostimulation systems and methods of treating migraine headaches and other forms of chronic head pain.

BACKGROUND OF THE INVENTION

Neurostimulation systems comprising implantable neurostimulation leads are used to treat chronic pain. Conventional implantable peripheral neurostimulation leads are designed for placement in the spinal canal as part of a spinal cord stimulation system, and for the therapeutic purpose of treating various forms of chronic back and extremity pain.

SUMMARY OF THE INVENTION

In various implementations, an implantable neurostimulation lead designed for implantation in the head may include an extended lead body having a plurality of internal electrically conducting metal wires running along at least a portion of its length; a distal extended surface metal electrode array, and a proximal in-line connector. The extended lead body may comprise a medical grade plastic. The electrode array may be subdivided into a plurality of sub-arrays. In some implementations, the electrode array is subdivided into three or more sub-arrays. The proximal in-line connector may include a proximal surface contact array adapted to couple with an implantable pulse generator.

Implementations may include one or more of the following features. A single lead may include a plurality of surface electrodes along its length to provide therapeutic stimulation over the frontal, parietal, and occipital regions of the hemicranium substantially simultaneously. The lead may not require a central channel for stylet placement over its distal (frontal) portions. The lead may have a flattened lead design for that portion of the lead expected to be positioned over the frontal region of the head. At least one portion of the lead may have a progressively tapered diameter. The single lead may be of sufficient length to reach a pulse generator located in a patient's body.

The single lead may include an electrode array operable to provide medically acceptable neurostimulation coverage over the supraorbital, auriculotemporal, and occipital nerves unilaterally. The electrode array may be divided into a plurality of sub-arrays such that, when the neurostimulation lead is implanted, at least one sub-array may be positioned over the frontal region, at least one sub-array may be positioned over the parietal region, and at least one sub-array may be positioned over the occipital region. The design of each sub-array may vary. In some implementations, the number of electrodes, the shape of the electrodes (i.e. cylindrical, flattened), the width of the electrodes, and/or the linear distance separating the electrodes within each sub-array may vary.

In various implementations, methods of treating chronic pain may include methods of treating chronic head and/or face pain of multiple etiologies, including migraine headaches; and other primary headaches, including cluster headaches, hemicrania continua headaches, tension type headaches, chronic daily headaches, transformed migraine headaches; further including secondary headaches, such as cervicogenic headaches and other secondary musculoskeletal headaches.

In various implementations, methods of treating chronic pain may include methods of treating head and/or face pain of multiple etiologies, including neuropathic head and/or face pain, nociceptive head and/or face pain, and/or sympathetic related head and/or face pain.

In various implementations, methods of treating chronic pain may include methods of treating head and/or face pain of multiple etiologies, including greater occipital neuralgia, as well as the other various occipital neuralgias, supraorbital neuralgia, auroiculotemporal neuralgia, infraorbital neuralgia, and other trigeminal neuralgias, and other head and face neuralgias.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding, reference is now made to the following description taken in conjunction with the accompanying Drawings in which:

FIG. 1 depicts a side view of a complete neurostimulator lead for migraine and other head pain, demonstrating a plurality of electrodes in a distribution and over a length to allow full unilateral coverage of the frontal, parietal, and occipital portions of the head;

FIG. 2 depicts a side view of a Terminal Electrode Array over the Tapered Distal Lead Body and the Flattened Terminal Lead Body. Emphasis here is given to the progressive decrease in lead diameter over this portion of the lead to a very thin band like flattened terminal lead body, which is the portion of the lead typically located over the forehead;

FIG. 12 depicts a cross sectional side view of a Schematic Depiction of Flattened Terminal Lead Body In-Situ Compared with Current Standard Cylindrical Body. This figure provides graphic support for clinical benefits due the small-flattened portions, including better patient comfort and cosmetics. A schematic of the Mechano-thermal Flattening Process to achieve this flattened portion is described. This is only one of several possible methods of manufacture and is shown for illustrative purposes primarily; and FIG. 13 depicts a front view of a Legend for Figures.

INDEX OF ELEMENTS

Figure 3:
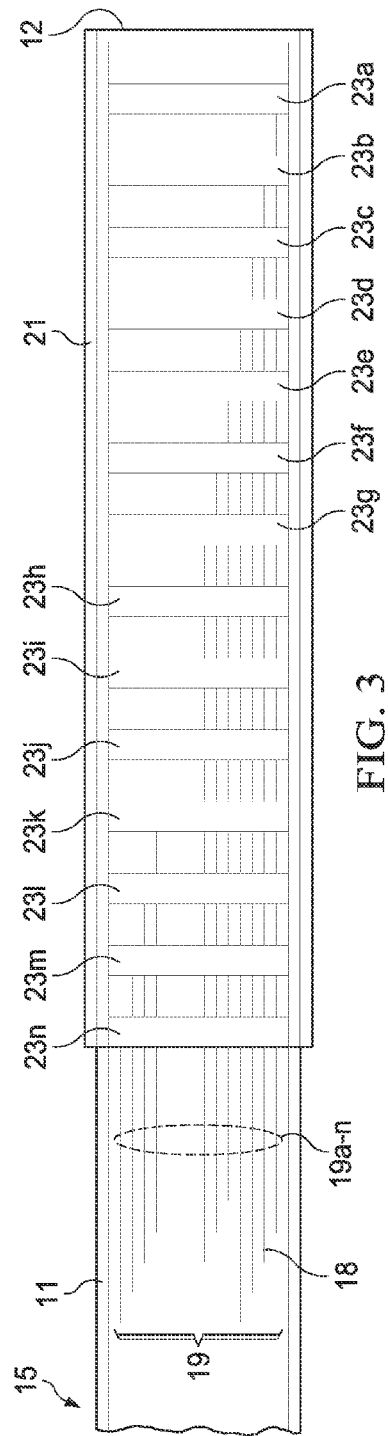
FIG. 3 depicts a side view of a Proximal In-line Connector (PIC) comprising a strengthened plastic layer over the basic lead body; a series of lead surface metal contacts; and the proximal portions of the lead body's metal conducting wires and proximal conducting links.

10: Lead Body.
11: Plastic Body Member
12: Proximal End
13: Distal End
14: Proximal Lead Body
15: Central Lead Body
16: Tapered Distal Lead Body (TDLB)
17: Flattened Terminal Lead Body (FTLB)
18: Internal Wire
19: Group of All Internal Wires
20: Proximal In-line Connector
21: Semi-rigid Plastic Cover
22: Surface Metal Contact
23: Proximal Contact Array
30: Terminal Electrode Array (TEA)
31: Surface Metal Electrode
32: Proximal Electrode Array (PEA)
33: Middle Electrode Array (MEA)
34: Distal Electrode Array (DEA)

DETAILED DESCRIPTION

A. Introduction

Referring now to the drawings, wherein like reference numbers are used herein to designate like elements throughout, the various views and embodiments of implantable neurostimulation lead for head pain are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

The present disclosure provides for an implantable neurostimulator lead that is operable for implantation in the head, and for the therapeutic purposes of treating migraine headaches and other forms of chronic head pain.

Prior implantable peripheral neurostimulation leads have been designed and developed specifically for placement in the spinal canal as part of a spinal cord stimulation system, and for the specific therapeutic purpose of treating various forms of chronic back and extremity pain. The present disclosure provides an implantable peripheral neurostimulation lead that is designed for the implantation in the head for the treatment of chronic head pain. It incorporates multiple unique elements and features that take into account the unique anatomic, physiologic, and other related challenges of treating head pain with implantable neurostimulation and by doing so greatly improves on therapeutic response, patient safety, medical risk, and medical costs, which combine to improve overall patient satisfaction.

Prior neurostimulator leads for the treatment of head pain by peripheral neurostimulation were designed and manufactured specifically for placement in the spinal canal for the treatment of chronic back and extremity pain. The anatomy of the head, and the pathophysiology of headaches and other forms of head pain that are unique to the head, are so significantly different from the anatomy of the spinal canal, and pathophysiology of chronic back pain that when these current leads are indeed utilized as cranial implants, then the clinical problems associated with these differences manifest themselves. Specifically, these include issues with inadequate therapeutic responses, issues with patient comfort and cosmetics, and also very significant issues with patient safety. These medical risks stem from the problem of commonly having to implant multiple (often four or more) of the currently available leads in order to adequately cover the painful regions of the head. These leads are also larger in diameter than what would be desirable for peripheral stimulation leads implanted in the head, and the cylindrical form of the leads results in extra pressure on the skin overlying the lead, which results in extra pressure on the skin. From a cosmetic perspective, the cylindrical leads often leave a line or wrinkle over the forehead due the pressure from the subcutaneous course of the cylinder on the overlying skin. In addition, prior leads are often of inadequate length to extend from the head to the gluteal region, which is a common site for implantation of the pulse generator. This necessitates the employment of surgically implanted lead extensions, a solution that brings with it another set of risks to the patients with the most common risks being that of infection due an increased number of incisions, and local discomfort due the relatively large size of the extension connections.

With respect to prior leads: 1) There is only a single array of electrodes, with common lead options including 4, 8, or 16 electrodes disposed over that single array; 2) The array is relatively short with most leads having an array of from 5-12 cm in length; 3) Within this single array, the individual electrodes are disposed uniformly with constant, equal inter-electrode distances of from approximately 2 to 10 mm.

There are several practical clinical outcomes that result from the use of prior leads for the treatment of chronic head pain. First, since they comprise a single, relatively short active array, the currently available leads provide therapeutic stimulation to only a single region of the head; that is, they can provide stimulation to only the frontal region, or a portion of the parietal region, or a portion of the occipital region. Therefore, if a patient has pain that extends over multiple regions, then multiple separate lead implants are required—basically one lead implant is required for each unilateral region. A great majority of patients with chronic headaches experience holocephalic pain; that is they experience pain over the frontal and parietal and occipital regions bilaterally. Therefore, commonly these patients will need 4 to 7 leads implanted to achieve adequate therapeutic results (2 or 3 leads on each side).

Second, the need for multiple leads includes considerable added expense, and more importantly, added medical risk associated with adverse events attendant to the multiple surgical procedures. Such adverse events include an increased risk of infection, bleeding, and technical issues with the leads, e.g., lead fracture, lead migration, and local irritation.

Third, as the clinical database discloses, the inter-electrode spacing may be of central therapeutic significance. That is, for example, whereas commonly pain over the occipital region is consistently effectively treated by quadripolar leads (leads with four evenly spaced electrodes) that have the electrodes relatively widely spaced apart (approximately a cm or more apart), clinically it is often found that electrode configurations that are more narrowly spaced may be more effective over the supraorbital nerve and regions. Thus, a quadripolar lead that has the electrodes only 1-2 mm apart may be more effective in this region, as it allows for more precise control of the delivered electrical pulse wave delivery.

The present disclosure is directed to an implantable neurostimulation lead that is customized and optimized for implantation in the head, and for the purpose of treating migraine headaches and other forms of chronic head pain, including chronic migraine and other headaches, as well as other forms of head pain.

The present disclosure addresses and effectively solves problems attendant to publically available leads. The most important of these is the fact that current leads can only adequately stimulate a single region of the head due to design element flaws associated with terminal surface electrode number and disposition. The disclosure additionally addresses and solves other problems inherent with the currently available leads, including problems with cosmetics and patient comfort, particularly over the frontal regions, due the uncomfortable pressure placed on the skin of the forehead, due the cylindrical shape and relatively large diameter of the distal portion of the lead. Finally, the lead of the present disclosure solves the currently available leads' problem of inadequate lead length to reach a gluteal location of the implantable pulse generator, which therefore necessitates the additional risk and expense of further surgery to implant lead extensions.

Thus the present disclosure provides for a peripheral neurostimulation lead that is uniquely designed for implantation in the head as a therapy for chronic head pain, and is designed to solve the known design issues associated with current leads, as the lead of the present disclosure seeks to optimize the therapeutic response, improve patient comfort, improve cosmetics, reduce the number of surgical leads required, and reduce medical risk. By reducing the number of leads, and the number of subsequent surgeries required for untoward events, medical costs are also markedly reduced.

In one aspect, the Implantable Peripheral Neurostimulation Lead for Head Pain is operable for implantation in the head, and to provide neurostimulation therapy for chronic head pain, including chronic head pain caused by migraine and other headaches, as well as chronic head pain due other etiologies. The peripheral neurostimulator lead disclosed herein takes into account unique anatomic features of the human head, as well as the unique, or singular, features of the various pathologies that give rise to head pain, including migraine and other headaches, as well as other forms of chronic head pain. This lead design for implantation in the head for chronic head pain recognizes that thus far all commercially available leads that have been clinically utilized for implantation as a peripheral neurostimulator lead were actually originally designed specifically for placement in the epidural space, as part of a spinal cord stimulation system, for the therapeutic purpose of treating chronic back and/or extremity pain. Thus, there are currently no commercially available leads, or leads that have designs in the public domain, that have been designed and developed for use in the head and for head pain.

In another aspect, the Implantable Peripheral Neurostimulation Lead For Head Pain comprises multiple design features, including disposition of a sufficient plurality of surface electrodes over a sufficient linear distance along the distal lead, such as will result in lead that, as a single lead, is capable of providing medically adequate therapeutic stimulation over the entire hemicranium; that is, over the frontal, parietal, and occipital region simulations. Currently available leads, which were designed specifically for epidural placement for chronic back pain, are capable of only providing stimulation over a single region; that is over either the frontal region alone, or the parietal region alone, or the occipital region alone.

In yet another aspect, the Implantable Peripheral Neurostimulation Lead for Head Pain comprises multiple design features, including the physical grouping of the extended array of surface electrodes into three or more discrete terminal surface electrode arrays. The linear layout of these two or more (preferably three or more) surface electrodes arrays is designed such that following implantation there would be at least one array positioned over the frontal region, at least one array positioned over the parietal region, and at least one array positioned over the occipital region. This feature further improves upon therapeutic effectiveness of the extended terminal surface electrode array sufficient for hemicranial stimulation by allowing for more precise control of the therapeutic neurostimulation parameters.

In still another aspect, the Implantable Peripheral Neurostimulation Lead For Head Pain comprises multiple design features, including incorporating individual design features within each of the three or more individual surface electrode arrays; examples of such intra-array design features would include the specific number of electrodes allotted to each group; whether the electrodes are cylindrical or flattened; the width of each electrode within each array, and the linear distance intervals of separation of the electrodes within each array. This feature further improves upon therapeutic effectiveness of the extended terminal surface electrode array sufficient for hemicranial stimulation, and the grouping of these electrodes into three or more separate surface electrode arrays, by providing each specific array location a unique intra-array design that takes into account, and thereby seeks to optimize design elements that are known to be possibly or likely beneficial to the therapeutic end result, given the anticipated post-implant anatomic location of that array.

In yet another aspect, an Implantable Peripheral Neurostimulation Lead for Head Pain comprises multiple novel design features, including incorporating individual design features into a single lead design and thereby achieving additive benefits.

In still another aspect, an Implantable Peripheral Neurostimulation Lead for Head Pain results in a marked decrease in the number of separate lead implants required to adequately treat a single patient. A single implant will provide the same therapeutic anatomic coverage that it would take the implantation of three or four of the currently available leads; that is instead of the current which often calls for three or more leads to be implanted to provide adequate hemicranial coverage, the same anatomic region may be covered with a single stimulator lead implant. The lead provides extended coverage over the full hemicranium; that is achieving medically acceptable neurostimulation unilaterally over the frontal, parietal, and occipital regions simultaneously. In contrast, publically known leads are able to consistently provide medically acceptable neurostimulation therapy only over a single region; meaning that it would require three separate surgically lead implants to achieve the same therapeutic coverage of a single implant of a lead of the present disclosure.

In another aspect, an Implantable Peripheral Neurostimulation Lead For Head Pain comprises multiple design features; including features aimed at improving patient safety by improving the incidence of adverse events, including the risk of infection, as well as the risk and incidence of known technical problems associated with implanted leads, including lead migration and lead fracture, amongst others. The lead may comprise two or more (i.e. three or more) surface electrode arrays, each uniquely designed, that are disposed over a sufficient lead length to allow for medically acceptable therapeutic neurostimulator coverage of at least regions within the supraorbital, parietal, and occipital cranial regions. To achieve the same clinical coverage from a single implant, it would require three or more separately surgically implanted leads. Therefore, by reducing the number of surgical incisions, as well as the number of surgically implanted leads, the associated risks of adverse events are proportionally diminished.

In yet another aspect, an Implantable Peripheral Neurostimulation Lead For Head Pain may treat chronic head and/or face pain of multiple etiologies, including migraine headaches; and other primary headaches, including cluster headaches, hemicrania continua headaches, tension type headaches, chronic daily headaches, transformed migraine headaches; further including secondary headaches, such as cervicogenic headaches and other secondary musculoskeletal headaches; including neuropathic head and/or face pain, nociceptive head and/or face pain, and/or sympathetic related head and/or face pain; including greater occipital neuralgia, as well as the other various occipital neuralgias, supraorbital neuralgia, auroiculotemporal neuralgia, infraorbital neuralgia, and other trigeminal neuralgias, and other head and face neuralgias.

In other aspects, an Implantable Peripheral Neurostimulation Lead for Head Pain may not require a central channel for stylet placement over its distal (frontal) portions. The lead may improve patient comfort and cosmetics by virtue of its relatively small diameter over the distal portions of the lead, partially due the lack of a central stylet channel, as well as due to a progressive decrease in the number of internal wires continuing after each terminal electrode. The lead may further improve cosmetic appearance and patient comfort by incorporating a flattened lead design for that portion of the lead expected to be over the frontal portion of the head. The lead may be compatible with currently available implantable pulse generators. The lead may incorporate an electrode array design that is capable as a single lead of providing medically acceptable neurostimulation coverage over the supraorbital, auriculotemporal, and occipital nerves unilaterally. The lead may be of sufficient length to adequately reach all common pulse generator locations, thereby potentially obviating the need for lead extensions and in turn decreasing the risk of problems attendant to such extensions, including discomfort, infection, technical extension issues such as fracture, and other morbidities. The single lead may be operable to provide medically acceptable neurostimulation coverage that treats head pain over the frontal, lateral, and posterior regions. The single lead may be operable to provide medically acceptable therapeutic neurostimulation coverage that would otherwise often require unilateral leads (six total leads if, as is common the pain is global/holocephalic), thereby resulting in a decrease in the number of patients that require more than one associated Implantable Pulse Generator (IPG). Currently available IPGs are capable of accepting a maximum of four leads, each having the ability to cover only one anatomic region, as each lead only has one active array. The lead may include a progressively tapering diameter over the lead segment containing the three active arrays, a feature serving clinical improvements in patient comfort and cosmetics. The lead may further comprise a distal array disposed over a thin, flattened terminal portion of the lead, which is the portion intended to be positioned over the supraorbital (frontal) region, a feature serving clinical improvements in patient comfort and cosmetics.

B. Overview

Turning now descriptively to the drawings, the first eight of which depict the lead in various aspects and view, in which similar reference characters denote similar elements throughout the several views. The figures illustrate an extended lead body, comprised of a medical grade plastic, and a plurality of internal electrically conducting metal wires running its length; a distal extended metal surface electrode array, subdivided into three or more sub-arrays; and a proximal in-line connector, which contains a proximal surface contact array, for mating with a separate implantable pulse generator.

Following the eight drawings of various aspects of the lead come three drawings depicting the lead in-situ in the human head, including posterior, side and frontal views.

Finally is a drawing set that serves to pictorially illustrate some additional benefits of the lead design, specifically improvements in cosmetics and patient comfort specifically related to the design of the flattened distal lead body and its associated distal lead array.

C. Full Neurostimulator Lead

FIG. 1 depicts a side view of a completely assembled lead, which is comprised of three main elements—a lead body 10; a proximal in-line connector 20; and a terminal electrode array 30.

D. Lead Body

Continuing with FIG. 1, the lead body 10 is itself comprised of two primary components—the plastic body member 11 and a set of internal metal conducting wires(s) 18 (19).

Figure 6:
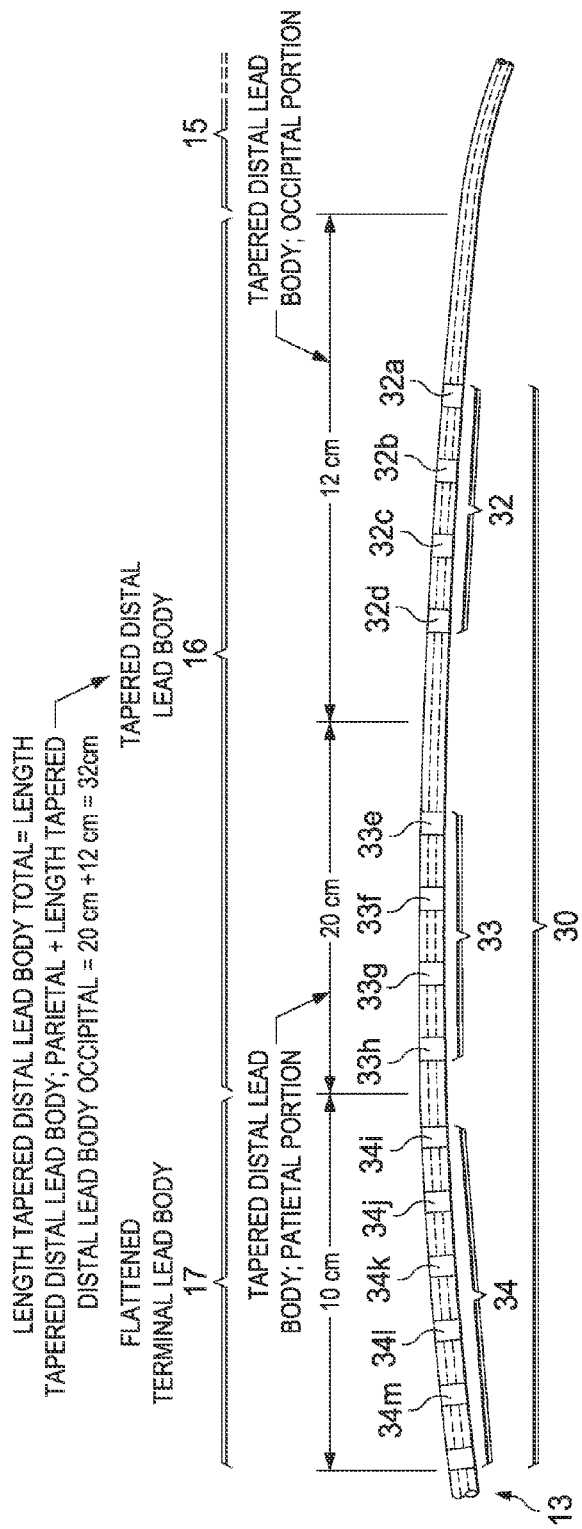
FIG. 6 depicts a side view of the Terminal Electrode Array (TEA) and the Tapered Distal Lead Body and Flattened Terminal Lead Body. The electrodes of the TEA divided into the Proximal, Middle, and Distal Electrode Arrays (each with a plurality of electrodes) is over a total distal lead portion to ensure electrode coverage of the frontal, parietal and occipital regions of the head unilaterally. This would entail positioning the electrodes at various intervals over the distal portion (such as 35-45 cm) of the lead.

The plastic body member 11 is an elongated, cylindrical, flexible member, which may be formed of a medical grade plastic polymer. It has a proximal end 12 and a distal end 13. The total length of the lead body is subdivided on the basis of multiple parameters, including importantly lead diameter and lead shape, into four contiguous portions—which, progressing from the proximal end 12 towards the distal end 13 include sequentially a proximal lead body 14; a central lead body 15; a tapered distal lead body 16; and finally a flattened terminal lead body 17 that terminates at its distal end 13 (FIG. 6, 7). The proximal lead body 14 and the central lead body 15 are cylindrical in shape and of constant diameter throughout their portions, which are standard features of the currently available leads. The tapered distal lead body 16 continues with this cylindrical shape; however, beginning near its proximal junction with the central lead body 15, the diameter of the tapered distal lead body 16 progressively decreases to a minimum near its junction with the terminal flattened lead body 17. While having a relatively constant cross-sectional area along its length that is roughly the same as the minimum cross sectional area of the distal tapered distal lead body 16, the foundational feature of the flattened lead body is its thin, flattened, ribbon-like shape that is generally constant along its entire length.

Housed in the plastic body member 11 is a plurality of individual, longitudinal metal internal wires 18, which collectively form a set of all internal wires 19. Each individual wire (19 a-n) of this set originates at a prescribed location on the surface of the proximal lead body. It then passes down into, and then lengthwise along, the core of the plastic body member 11 until it nears its prescribed distal terminus, at which point it curves up to a specific point on the surface on one of the distal portions of the lead—either the tapered distal lead body 16, or the flattened terminal lead body 17. Viewed differently, the proximal and distal tips of each individual wire (19 a-n) are at specific, predetermined points along the surface of the lead, and between these points the lead wire passes lengthwise along the core of the lead body. In this embodiment there are fourteen internal wires (19 a-n).

There are two related features: first, is having the an extended TEA 30 that is capable of providing neuro stimulation over an entire hemicranium; that is over either the left or right side of the head (e.g. the left occipital region, parietal region and supraorbital region to the midline). This is achieved by ensuring that the lead is comprised of a sufficient plurality of electrodes over such an extended course of the lead body (the TDLB 16 and the FTLB 17), as to allow for two or more electrodes that are positioned over the portion of the lead that covers the supraorbital region 61 (the FTLB 17), two or more electrodes that are positioned over the portion of the lead that covers a portion of the parietal lead region 62 (the TDLB 17; Parietal Portion), and two or more electrodes that are positioned over the portion of the lead that covers the occipital region of the head 63 (the TDLB 17; Occipital Portion). While 2 electrodes over each region is the minimal requirement, it is preferable to have 4-8 or more electrodes over each region. In this embodiment there are 6 electrodes over the frontal region (FTLB 16); 4 electrodes over the parietal region (TDLB 16; Parietal Portion); and 4 electrodes over the occipital region (TDLB 16; Occipital Portion).

Figure 5:
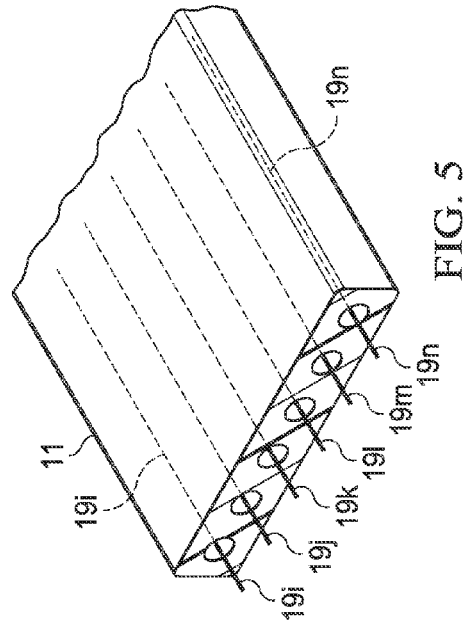
FIG. 5 depicts a cross sectional view of a Distal Flattened Terminal Lead Body in which the distal terminal portion (such as 8-12 cm) of the lead is flattened to allow for better cosmetics and comfort, noting this portion of the lead will typically be over the forehead. This is contrasted to the lead central body and the tapered distal lead body, which are both cylindrical and larger in diameter, but are intended to be surgically positioned over the posterior and side portions of the head respectively.
Figure 4:
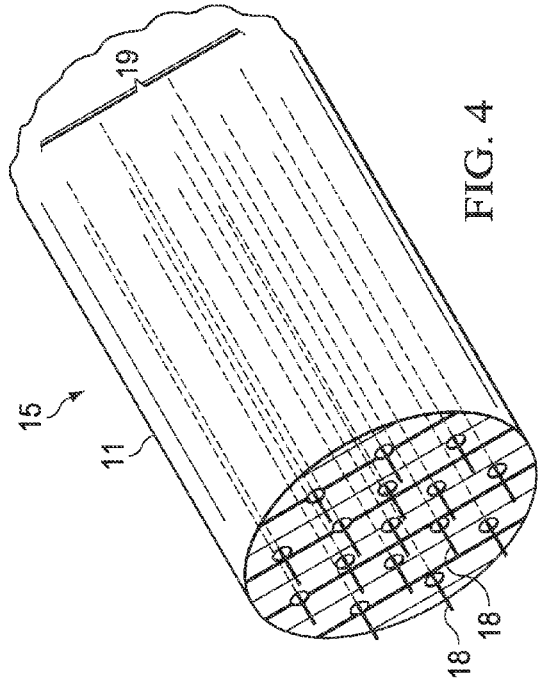
FIG. 4 depicts a cross sectional view of a Lead Central Body comprising a cylindrical lead body (with internal wires) between the Proximal In-line Connector and the Tapered Distal Lead Body.
Figure 9:
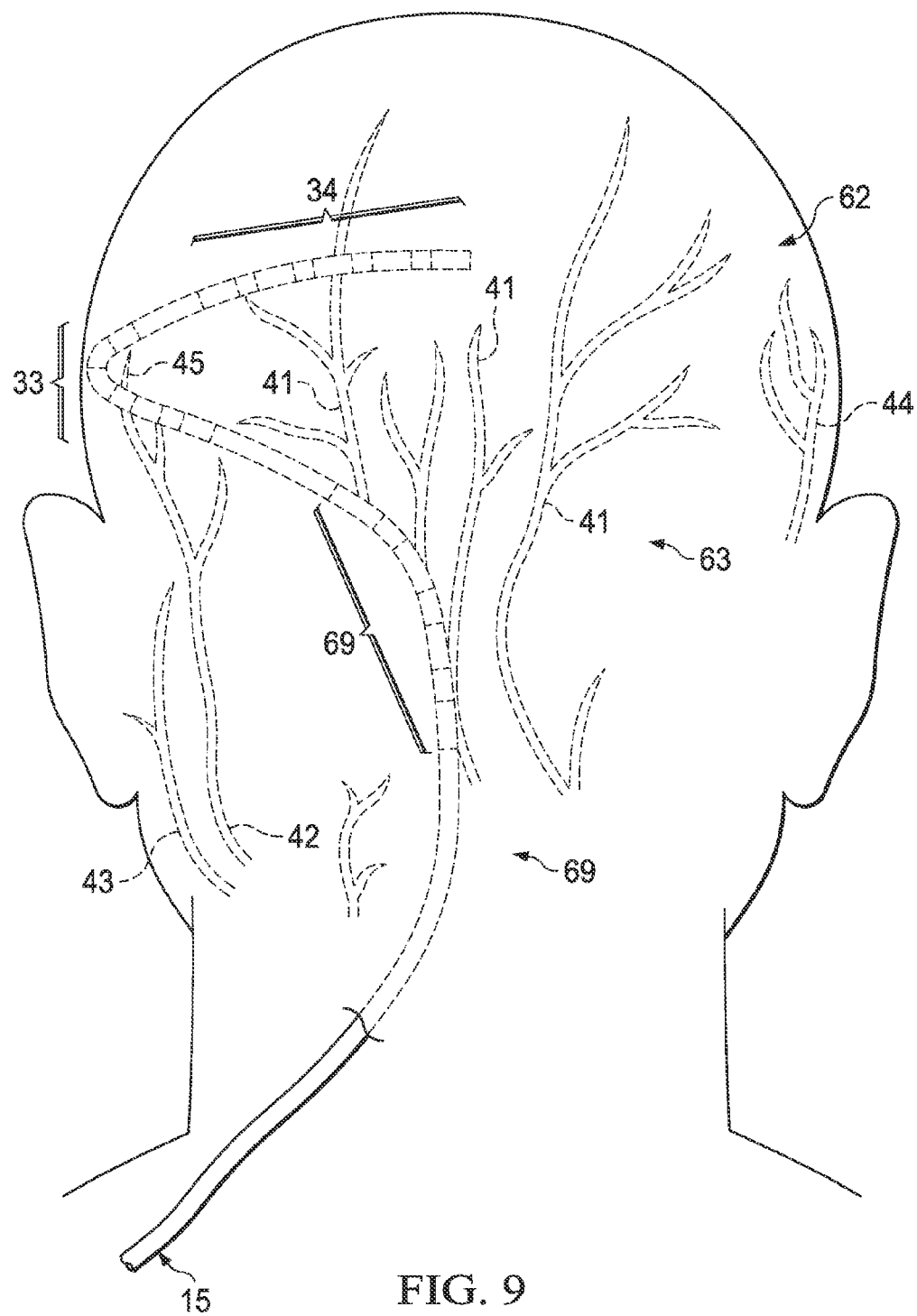
FIG. 9 depicts a rear view of a Head with Full Lead In-Situ. The lead is depicted passing up the posterior aspect of the neck, where beginning in the left mid-occipital region, the Terminal Electrode Array begins. The three electrode array divisions of the TEA are depicted as covering the left occipital, parietal, and supraorbital (frontal) regions to the midline of the forehead.
Figure 10:
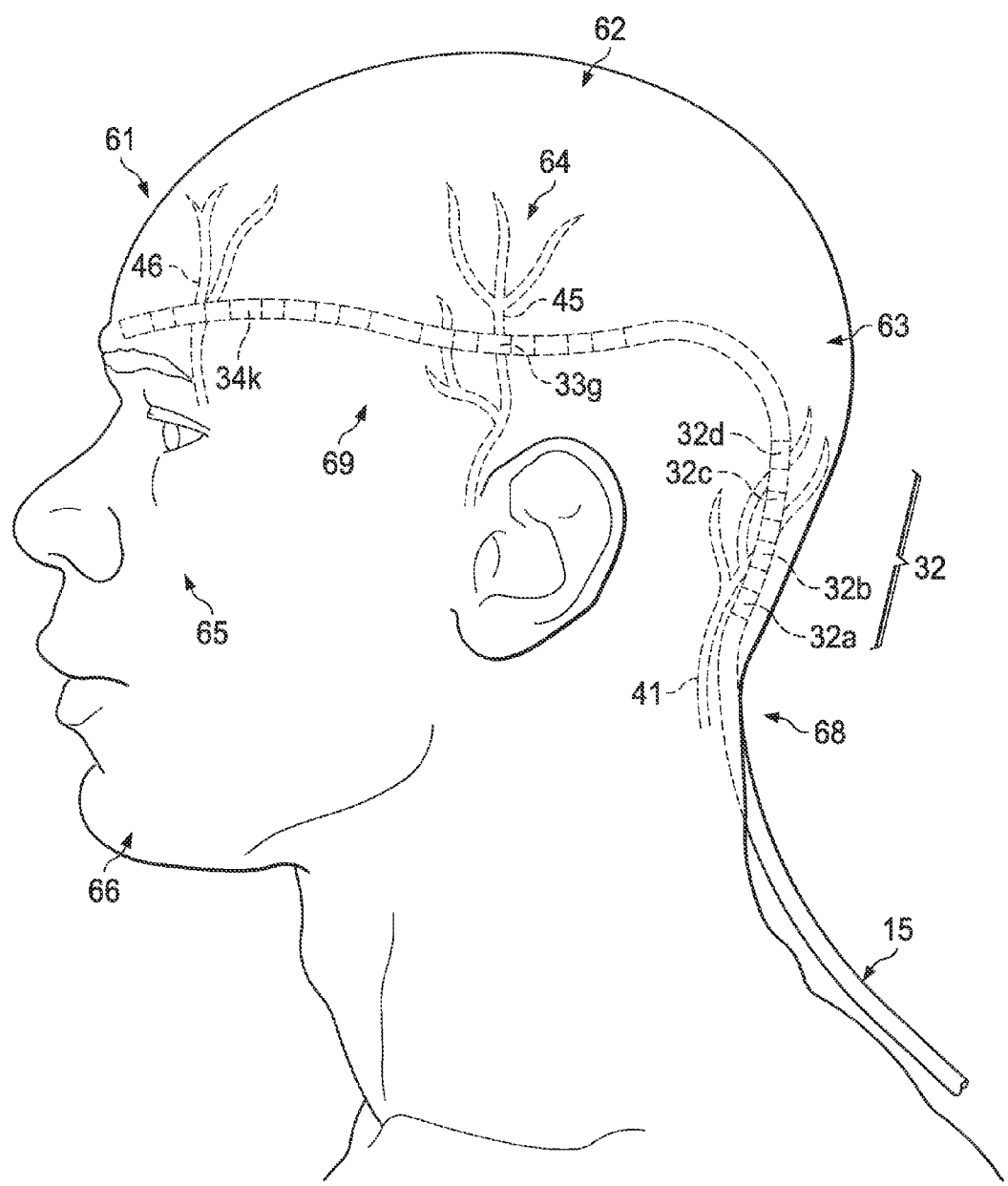
FIG. 10 depicts a side view of a Head with Terminal Electrode Array In-Situ. This lateral view also depicts the lead passing up the posterior aspect of the neck, where beginning in the left mid-occipital region, the Terminal Electrode Array begins. The three electrode array divisions (proximal, middle, and distal) of the TEA are depicted as covering the left occipital, parietal, and supraorbital (frontal) regions, along with the major associated nerves, to the midline of the forehead.
Figure 11:
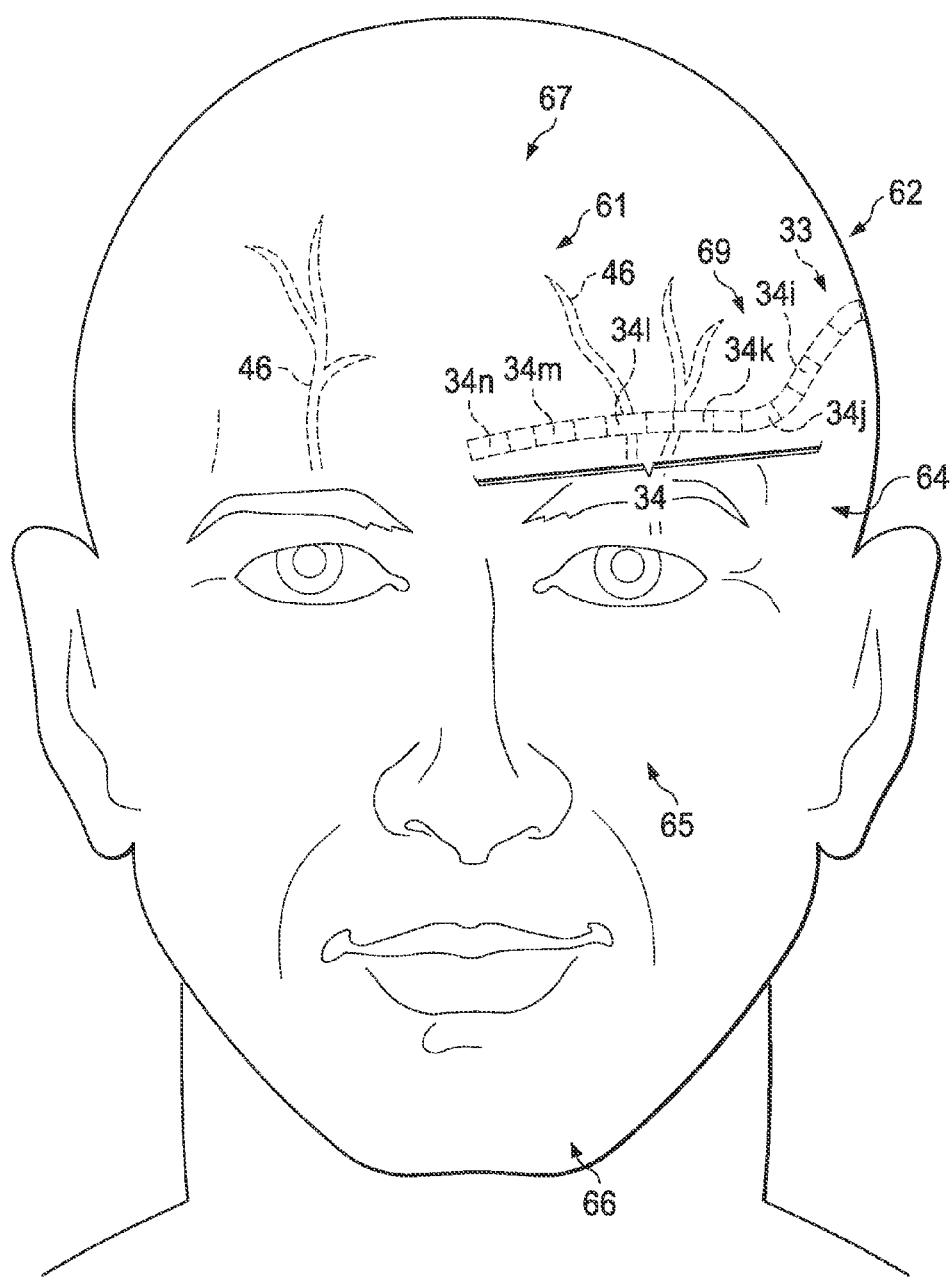
FIG. 11 depicts a front view of a Head with Distal Portion of the Terminal Electrode Array In-Situ. This frontal view depicts primarily the course of the Flattened Terminal Lead Body and its associated Distal Electrode Array in classic position over the left supraorbital region, where it extends to the midline. The associated major nerves of the region are depicted.

The measured lengths of the distal portions of the lead body (TDLB 16, FTLB 17) over which the terminal electrode array 30, along with its three sub-arrays (PEA 32, MEA 33, DEA 34), are disposed is determined as depicted in FIG. 5. Basically, for this measurement the lead is considered to be correctly surgically positioned, as illustrated in FIGS. 9, 10, and 11, such that the distal end is at the vertical midline of the forehead 67, whereupon the lead passes immediately posteriorly over the parietal region 62, passing just over the right ear towards the occiput and then down towards a meeting point at the midline C1 level 68. Thus, positioned the total length is that length of the lead measured from the distal end to the point where the lead reaches the C1 midline 68. This length should equal the sum of the separate lengths of the TDLB 16 and FTLB 17 portions of the lead. Referring back to FIG. 5, this total length, the component length of the FTLB 17 must be sufficient to reach from the distal end to the junction of the lateral edge of the forehead and the anterior edge of the parietal region 69. The component length of the TDLB 16 should be approximately equal to the distance from the lateral edge of the forehead to the C1 midline point. These lead sub-length requirements allow for one of the novel elements of the disclosure, namely that the lead is capable of disposing surface metal electrodes 31 anywhere along a line running from the mid-forehead (supraorbital region 61), over the parietal region 62, and then across the occipital region 63 to the midline C1 level 68. This therefore allows for treatment of head pain along this length, or head pain over the frontal (supraorbital 61), parietal 62, and occipital 63 regions with one lead.

Generally, the DEA 34 is positioned over the FTLB 17 (subserving pain therapy for the supraorbital region 61); the MEA 33 over the TDLB 16; distal portion (subserving pain therapy for the parietal region 62); and the PEA 32 over the proximal TDLB 16; proximal portion (subserving pain therapy for the occipital region 63).

E. Proximal in-Line Connector

Referring again to FIG. 1, the PIC 20 comprises three sub-units—the proximal lead body 14, a semi-rigid plastic cover 21 that covers the proximal lead body 14, and the proximal contact array 23. The PIC 20 is designed to mate with an implantable pulse generator.

Referring to FIG. 3, the fundamental component of the proximal contact array 23 is a surface metal contact (SMC) 22. A SMC 22 is a well-known, common element of neurostimulation leads and may be manufactured by standard processes, including electroplating, out of several common, standard conducting metals. Dimensions of commonly available electrodes may range considerably often being 1-2 mm (or less in width) and of thickness to less than 0.1 mm. It is molded and affixed to a position along the PIC 23 with the surface of the electrode generally being flush with the surface of the PIC 23. The specific surface positions of the electrodes correspond to the proximal surface tips of internal lead wires 19, such that as part of the process of molding and attaching the electrodes 22, each is physically and functionally mated to the underlying lead internal wire 18. The proximal contact array 23 is comprised of all of the individual surface metal contacts 22 *a-n*. In this embodiment there are 14 surface metal contacts 22 that comprise the proximal contact array 23.

F. Terminal Electrode Array

The terminal electrode array (TEA) 30 comprises a conducting surface metal electrode (SME) 31. A SME 31 is a well-known, common element of neurostimulation leads and may be manufactured by standard processes, including electroplating, out of several common, conducting standard metals. Dimensions of commonly available electrodes may range considerably, with example ranges of width as from 2 to 10 mm, and of thickness to less than 0.1 mm. It is molded and affixed to a position along the distal tapered body lead (DTBL) 16 and/or the terminal flattened body lead (TFBL) 17 portion of the plastic body member 11 with the surface of the electrode generally being flush with the surface of the plastic body member. The specific surface positions of the electrodes correspond to where the tips of the internal lead wires 19 surface, such that as part of the process of molding and attaching the electrodes 31, each is physically and functionally mated to the underlying lead internal wire 18.

Figure 8:
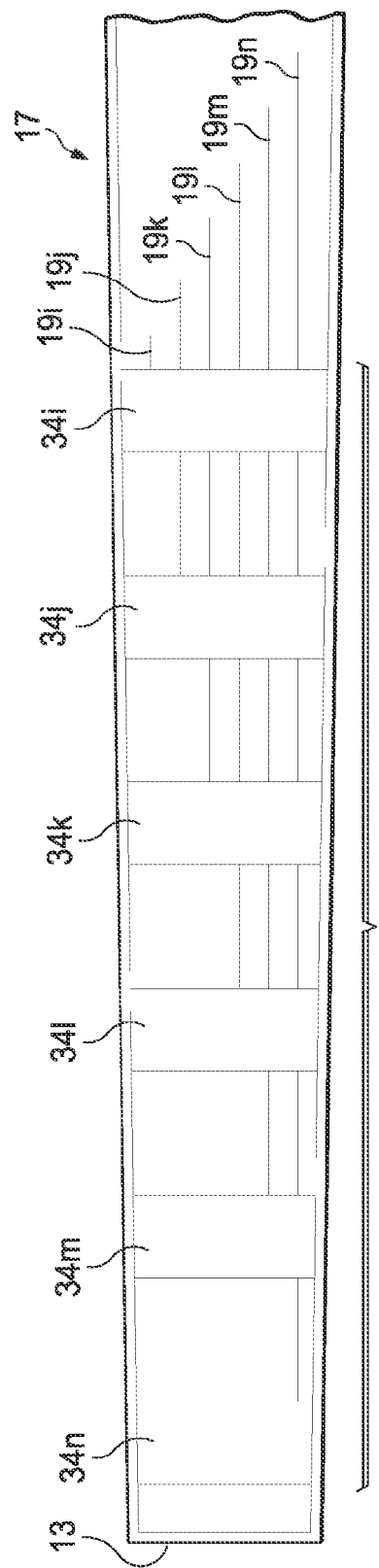
FIG. 8 depicts a side view of a Distal Electrode Array Over the Flattened Terminal Lead Body. This places the contact array over the distal portion (such as 8-12 cm) of the lead, which anatomically covers the supraorbital unilaterally (covers the forehead from the midline to the side of the forehead)

The TEA 30 comprises a plurality of these surface metal electrodes 31, which are disposed along certain distal portions of the plastic body member. The full plurality of electrodes of the TEA is sub-divided into a plurality of electrode sub-arrays, with the embodiment here consisting of 3 electrode arrays—the proximal electrode array (PEA) 32 (containing 4 surface metal electrodes 32 *a-d*); the middle electrode array (MEA) 33 (containing 4 surface metal electrodes 33 *e-h*) and the distal electrode array (DEA) 34 [FIG. 8] (containing 6 surface metal electrodes 34 *i-n*). The PEA 32 and the MEA 33 are disposed along the TDBL 16 section of the Plastic Body Member 11 (with the PEA 32 itself being proximal relative to the MEA 33 along the TDBL 16).

G. Connections of Main Elements and Sub-Elements

The overall mechanistic purpose of an implantable neurostimulation lead is to conduct an electrical pulse wave from its implantable pulse generator (IPG) down a set of lead wires 19 running a portion of the length of the lead to specific programmed sets of terminal surface electrodes 31, whereby the current is conducted by tissue and fluid to an adjacent, or nearby, set of one or more terminal surface electrodes, which in turn passes the signal proximally down the lead wire to its attached proximal terminal contact, which returns it to the pulse generator, completing the circuit.

Figure 7:
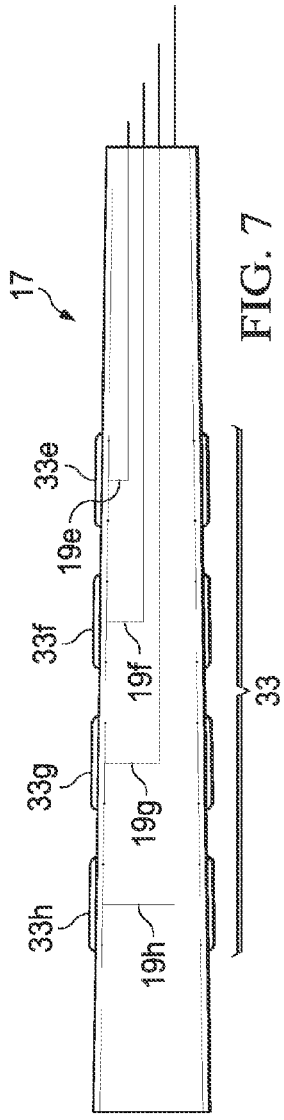
FIG. 7 depicts a side view of a Middle Electrode Array with Internal Wires. The Middle Electrode Array is disposed over the distal portion (such as 16-20 cm) of the Tapered Distal Lead Body, which anatomically places it over the parietal region of the head, which includes subregions such as the temple region innervated by the auriculotemporal nerve.

The foundational physical electrical unit of the system comprises a proximal surface metal contact 22, which is connected to the proximal end 12 of an internal wire of the lead [FIG. 3], which in turn has its distal end 13 connected to a distal surface metal electrode 31 electrode [FIG. 7].

Thus the contact-wire-electrode combination effectively provides a continuous metal conductor from the proximal contact to a distal contact.

The plastic body member 11 thus functions both as a physical conduit and an insulator for the fourteen internal lead wires 19, as well as a physical surface substrate for the fourteen attached proximal surface metal contacts 22 and distal surface metal electrodes 31. A complete lead, when mated with an IPG and appropriately implanted, such that the lead terminals are in the proximity of specific nerves to be stimulated, will be capable of effectively delivering an electrical pulse signal from the attached IPG to the distal terminals and to associated nerves targeted in the implant. This electrical stimulation of the nerves(s) forms the mechanistic foundation for the therapeutic effect. Additional functions of the plastic body member relates to its distal tapered portion and its terminal flattened portion, both of which serve for improved patient comfort and cosmetics.

In this embodiment the number (fourteen) of electrodes, internal wires, and contacts are equal. In other words the lead contains fourteen contacts that connect to the proximal ends of fourteen internal wires 19, which extend down the core of the plastic body member 11 to connect to fourteen terminal electrodes 31 on the TEA 30 with each wire connecting one contact and one electrode. Thus, there are fourteen foundational physical electrical units (surface metal contact internal wire-surface metal electrode (22-18-31)).

H. First Embodiment

The first embodiment provides for a lead that incorporates one or more of the features outlined above, including a tapered distal lead body 16, a flattened terminal lead body 17, and lacks a central stylet channel. The length is 120 cm, which is sufficient to reach a pulse generator implanted in the gluteal region.

The terminal electrode array 30 is comprised of 16 electrodes disposed over three separate electrode arrays. The distal electrode array (DEA) 34 is comprised of 6 electrodes, each 6 mm wide, positioned uniformly over 7 cm of the FTLB 17 portion of the lead with the most distal electrode ending 4 mm from the distal end 13. This allows for a short length of thin malleable soft plastic at the tip, which will decrease unwanted pressure on the skin overlying the tip. The middle electrode array (MEA) 33 is comprised of four 7 mm wide electrodes, each separated 7 mm from its neighbor(s) for a total MEA 33 length of 4.9 cm. The distal end of the distal electrode of this group will be located 7 cm from the tip of the lead, which thus places the interval over the most distal portion of the TDLB 16. The remaining four electrodes, which comprise the proximal electrode array (PEA) 32, are 9 mm wide with a constant length interval between neighbors of 1 cm, for a total PEA 32 length of 7.6 cm. The PEA 32 electrodes are disposed over the proximal portion of the TDLB 16 (as relative to the MEA 33). In this embodiment the electrode arrays are positioned to optimize the therapeutic neurostimulation over the supraorbital nerve 41 (of the supraorbital region 61 of the head), the auriculotemporal nerve 45 (in the parietal region 62), and the greater occipital nerve 46 (in the occipital region of the head 63).

I. Alternate Embodiments

There are multiple alternate embodiments that preserve the features of the neurostimulation lead and system disclosed herein, which include a terminal electrode array over an extended area of the cranium. The lead should provide medically acceptable neurostimulation over at least two regions. The lead may include two or more electrode arrays. In various embodiments, the spacing and dimensions of the electrode array(s) may be constant, or the electrode arrays may be specifically designed with respect to specific electrode type, dimensions, and layout for improving the therapeutic effectiveness. Thus, the disclosure comprises extended electrode array design (two or more regions by a single lead), and/or multiple arrays and optimized intra-array electrode dispositions.

Alternate embodiments would include variations in the total number of electrodes. At least two electrodes may be included per region, and the first embodiment calls for 14, but there is no absolute limit to the maxim number. Similarly, while the first embodiment calls for three electrode arrays, the disclosure contemplates two or even one array (so long as the array covered at least two regions). There is also no limiting maximum for the number of arrays. Also, there may be multiple variations of design within each separate array, including for example, variations in the number, dimensions, shape, and metal composition of the individual electrodes, as well as the distance and constancy of distance between electrodes within each array. Further, each array may have the same or completely different design.

The disclosure may include a flattened frontal lead portion, a tapering distal lead body, a total lead length sufficient to reach the gluteal region, and the absence of a central stylet channel solve; however, the disclosure the absence of one or more of these elements.

While the neurostimulation lead has been described for implantation as a peripheral neurostimulator in the head and for head pain, it is capable of being implanted and used as a peripheral nerve stimulator over other regions of the head and face than described above and also over other peripheral nerves in the body.

J. Operation

When functioning; that is when the proximal in-line connector of the lead is connected to an active implantable pulse generator; the electrodes of the terminal electrode array are programmed to function as anodes and cathodes. The generated electrical pulse wave then passes from a connected proximal surface metal contact, along the associated internal lead wire, and ultimately to its associated terminal surface metal electrode. The current then passes a short distance through the subcutaneous tissue to a contiguous, or nearby, electrode, whereby it passes back up the lead to its associated proximal metal contact, and then back to the pulse generator to complete the circuit. It is the generated pulse waves passing through the subcutaneous tissue between two terminal electrodes that stimulate the sensory nerves of the area. When active, the pulse generator is usually programmed to produce a continuous series of pulse waves of specified frequency, amplitude, and pulse width. It is this series of pulse waves actively stimulating a patient's locally associated nerves that underpins the therapeutic effect of the entire functional implanted units. Electrical pulse waves then pass from a connected proximal surface metal contact, along the associated internal lead wire, and ultimately to its associated terminal surface metal contact.

Thus the lead of the present disclosure effectively answers and solves the problems and limitations inherent with the currently available leads. As the current leads are limited to therapeutically stimulating only one cranial region, most patients require multiple leads, typically 4-6 or more (two or three on each side). The present disclosure provides a system for resolving this problem by treating the entire hemicranium with a single lead (two required for holocephalic pain), a solution that in addition to much more effectively treating the patients pain, it solves the additional problem of surgical risk associated with the multiple surgical implants associated with the multiple leads. The therapeutic effectiveness of the current embodiment is further enhanced by employing three separate electrode arrays with one in each region and specifically with one over each of the major nerves—the supraorbital nerve, the auriculo-temporal nerve, and the occipital nerve on that side. Further therapeutic enhancement and satisfaction follow the improved intra-array electrode disposition designs. The additional functions of the plastic body member relates to its distal tapered portion, its terminal flattened portion, its lack of a central stylet channel, and its length sufficient to reach a gluteal pulse generator without requiring surgical lead extensions, all of which variably serve patient comfort, cosmetics and satisfaction.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "an accumulator" includes a combination of two or more accumulators; and, reference to "a valve" includes different types and/or combinations of valves. Reference to "a compressor" may include a combination of two or more compressors. As another example, "coupling" includes direct and/or indirect coupling of members.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

It will be appreciated by those skilled in the art having the benefit of this disclosure that this implantable neurostimulation lead for head pain provides an implantable neurostimulation lead having a plurality of electrode arrays spaced along a portion of its length such that when neurostimulation lead is implanted, at least one electrode array is positioned over the frontal region, at least one electrode array is positioned over the parietal region, and at least one electrode array is positioned over the occipital region of the patient's cranium so that when the neurostimulation lead is connected to an implantable pulse generator, the single lead can provide medically acceptable neurostimulation coverage over the supraorbital, the auriculotemporal, and the occipital nerves unilaterally. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An implantable neurostimulation lead comprising:
   a lead body having a length with a proximal end and a distal end, the lead body further comprising contiguous portions including a proximal lead body portion, a central lead body portion and a distal lead body portion, wherein the distal lead body portion comprises:
      a tapered distal lead body proximate the central lead body portion and having a cross section that tapers along at least a portion of the length thereof toward the distal end thereof,
      wherein the distal lead body portion has an angle of taper that is greater than an angle of taper of the central body portion, and
      a terminal lead body on the distal end of the distal lead body portion and having a flat exterior surface;
   a plurality of electrode arrays spaced linearly on an exterior surface of the distal lead body portion, and not on the exterior surface of the central lead body portion, each electrode array having a plurality of electrodes spaced linearly along the distal lead body portion, a linear spacing between the plurality of electrode arrays is larger than a linear spacing between the plurality of electrodes in each of the electrode arrays, wherein the plurality of electrode arrays comprises at least a distal electrode array on the terminal lead body proximate to the distal end and at least a proximal electrode array on the tapered distal lead body proximate to the central lead body; and
   a plurality of internal conductive wires in the lead body wherein each wire of the plurality of internal conductive wires is connected to a different electrode of the plurality of electrodes and extends to the proximal end of the lead body.

2. The implantable neurostimulation lead of claim 1, wherein the distal electrode array is configured to be implanted and positioned in a patient proximate the supraorbital nerves and the proximal electrode array is configured to be implanted and positioned in the patient proximate to the occipital nerves.

3. The implantable neurostimulation lead of claim 2, wherein the plurality of electrode arrays further comprises a central electrode array linearly spaced from and between the distal electrode array and the proximal electrode array on the terminal distal lead body, the central electrode array is configured to be implanted and positioned in the patient proximate to the auriculotemporal nerve.

4. The implantable neurostimulation lead of claim 1, wherein a distal electrode spacing between electrodes in the distal electrode array is different from a proximal electrode spacing between electrodes in the proximal electrode array.

5. The implantable neurostimulation lead of claim 4, wherein the plurality of electrode arrays further comprises a central electrode array between the distal electrode array and the proximate electrode array on the distal lead body; and wherein a central electrode spacing between electrodes in the central electrode array is different from the distal electrode spacing.

6. The implantable neurostimulation lead of claim 1, further comprising a proximal connector at the proximal end of the lead body, the proximal connector comprising a plurality of metal contacts such that each one of the metal contacts is electrically connected to a different wire of the plurality of internal wires.

7. The neurostimulation lead of claim 1, wherein an angle of taper of the terminal lead body is less than the angle of taper of the portion of the distal lead body portion between the terminal lead body and the central lead body portion.

8. A head implantable neurostimulation lead, comprising:
   a group of conductive wires;
   a lead body having a length with a proximal end and a distal end; the lead body contains the group of conductive wires; the lead body comprises contiguous portions including a proximal lead body portion, a central lead body portion and a distal lead body portion;
   wherein the distal lead body portion comprises:
      a tapered distal lead body proximate the central lead body portion and having a cross section that tapers along at least a portion of the length thereof toward the distal end thereof,
      wherein the distal lead body portion has an angle of taper that is greater than an angle of taper of the central body portion, and
      a terminal lead body on the distal end of the distal lead body portion and having a flat exterior surface;
   the distal lead body portion includes a plurality of electrode arrays spaced from each other along a length of the distal lead body portion such that no electrode arrays or any portion thereof are disposed on the central lead body portion;
   each electrode array of the plurality of electrode arrays comprises at least two surface electrodes spaced in close proximity to each other,
   each surface electrode is connected to a different wire of the group of conductive wires,
   the plurality of electrode arrays comprises at least a distal electrode array on the terminal lead body proximate to the distal end and at least a proximal electrode array on the tapered distal lead body proximate to the central lead body portion.

9. The head implantable neurostimulation lead of claim 8, wherein the plurality of electrode arrays further comprises a central electrode array between the distal electrode array and the proximal electrode array.

10. The head implantable neurostimulation lead of claim 8, wherein the at least two surface electrodes of one of the plurality of electrode arrays are spaced at a different linear distance from each other than the at least two electrodes of a second one of the plurality of arrays.

11. The head implantable neurostimulation lead of claim 8, wherein the plurality of electrode arrays are spaced along the length of the distal lead body portion such that when the head implantable neurostimulation lead is implanted in a patient, the distal electrode array of the plurality of electrode arrays is adapted to be positioned proximate to a supraorbital cranial region of the patient and the proximal electrode array of the plurality of electrode arrays is adapted to be positioned proximate to the occipital cranial region of the patient.

12. The head implantable neurostimulation lead of claim 11, wherein a third electrode array of the plurality of electrode arrays is between the distal and the proximal electrode arrays and adapted to be positioned proximate to the parietal cranial region of the patient.

13. The head implantable neurostimulation lead of claim 8, further comprising a connector at the proximal end connected to the group of conductive wires and adapted to connect to a pulse generator.

14. The head implantable neurostimulation lead of claim 8, wherein the proximal lead body portion and the central lead body portion comprise a rounded exterior surface along their length.

15. An implantable peripheral neurostimulation lead configured for implantation in the head, the neurostimulation lead comprising:
 a lead body having a length, a proximal end adapted for connection to an implantable pulse generator and a distal end;
 a plurality of conductive wires internal to the lead body that extend from the proximal end at least a portion of the length; and
 a plurality of electrode arrays spaced from each other on a distal portion of the lead body, each of the plurality of electrode arrays comprising a plurality of surface electrodes spaced from each other, and each of the plurality of surface electrodes being connected to a different one of the plurality of conductive wires,
 wherein the distal portion of the lead body tapers toward the distal end, a terminal lead body of the distal portion of the lead body is flat, and at least a portion of a proximal portion of the lead body is rounded in cross section, and
 the plurality of electrode arrays comprises a distal electrode array on the terminal lead body proximate to the distal end and a proximal electrode array on the distal lead portion proximate to a central lead body.

16. The neurostimulation lead of claim 15, wherein the plurality of surface electrodes in one of the electrode arrays of the plurality of electrode arrays have a first spacing distance and wherein the plurality of surface electrodes in another electrode array of the plurality of electrode arrays have a second spacing distance, wherein the first spacing distance is different from the second spacing distance.

17. The neurostimulation lead of claim 16, wherein an angle of taper of the terminal lead body is less than an angle of taper of the portion of the distal lead body portion between the terminal lead body and the central lead body portion.

* * * * *